United States Patent [19]

Reed

[11] Patent Number: 4,783,989
[45] Date of Patent: Nov. 15, 1988

[54] VAPOR PRESSURE MEASUREMENT APPARATUS AND METHOD

[75] Inventor: Donald B. Reed, Plano, Tex.

[73] Assignee: Atlantic Richfield Company, Los Angeles, Calif.

[21] Appl. No.: 22,155

[22] Filed: Mar. 5, 1987

[51] Int. Cl.$^4$ .............................................. G01N 7/14
[52] U.S. Cl. ......................................... 73/64.2; 73/53
[58] Field of Search ..................... 73/64.2, 19, 53, 61.3

[56] References Cited

U.S. PATENT DOCUMENTS

| | | | |
|---|---|---|---|
| 3,103,809 | 9/1963 | Dye | 73/64.2 |
| 3,145,561 | 8/1964 | Thompson | 73/64.2 |
| 3,195,354 | 7/1965 | Douslin | 73/64.2 |
| 3,528,440 | 9/1970 | Plucker, III | 73/64.2 |
| 3,673,853 | 7/1972 | Griswold et al. | 73/64.2 |
| 4,164,137 | 8/1979 | Williamson | 73/79 |
| 4,393,689 | 7/1983 | Renon et al. | 73/64.2 |
| 4,543,819 | 10/1985 | Chin et al. | 73/64.2 |

OTHER PUBLICATIONS

Gibbs, Vapor-Liquid Equibliria from Total Pressure Measurement, Ind. Eng. Chem. Fundam, vol. 11, No. 3, 1972.

Primary Examiner—Stewart J. Levy
Assistant Examiner—Hezron E. Williams
Attorney, Agent, or Firm—Michael E. Martin

[57] ABSTRACT

Vapor pressure of liquid compositions is measured by a system having a cylinder member in which a reciprocal piston is disposed for movement to contain a sample of liquid and expand the chamber while measuring the pressure in the chamber until a substantially constant pressure is reached with increasing chamber volume. Liquid is circulated from a source such as a petroleum pipeline to the apparatus and continually through the expansible chamber in a retracted position of the piston. When a sample vapor pressure measurement is to be taken, the piston closes off a passage leading to the chamber and displaces liquid out of the chamber until a minimum volume is reached. The movement of the piston is then reversed to increase chamber volume while monitoring pressure and temperature to detect the onset of cavitation. Different samples of the same liquid may be taken while permitting the maximum volume of the chamber to vary with each sample so that a plot of maximum or equilibrium pressures can be obtained as a function of chamber size whereby extrapolation may be used to determine true vapor pressure of the composition.

10 Claims, 3 Drawing Sheets

VAPOR PRESSURE MEASUREMENT APPARATUS AND METHOD

BACKGROUND OF THE INVENTION

1. Field of the Invention

The present invention pertains to an apparatus for measuring the vapor pressure of various liquids, particularly complex hydrocarbon mixtures.

2. Background

It is often necessary to determine the vapor pressure of a liquid or liquid mixture to assist in controlling transport conditions of the liquid or certain process conditions involving the liquid or its vapor. In many crude oil pipelining operations, it is desirable and often necessary to transport other liquids mixed with the crude oil, such as, natural gasoline liquids. Accordingly, a relatively complex liquid mixture is formed under such transport conditions and the vapor pressure of such a mixture cannot be readily predicted but can only be determined by frequent measurements of the fluid being transported through the pipeline. Moreover, the true vapor pressure of a complex liquid mixture such as a mixture of crude oil and natural gasoline liquids may actually be a changing value since the vapor pressure of the so called lighter ends of the mixture will be lower at a given temperature than the heavier or more dense hydrocarbon materials.

Accordingly, it has been deemed desirable to provide an apparatus which can readily measure at least the cavitation pressure of a complex liquid mixture so that pumping operations and the like may be controlled to prevent cavitation and leakage of vapors from the transport network. On the other hand, knowledge of the true vapor pressure is important for certain processing or separating operations.

It is an object of the present invention to provide an improved apparatus and method for determining the cavitation pressure of a pure or complex liquid mixture as well as the vapor pressure of the mixture with accuracy and in a manner which provides for sampling the liquid mixture to be measured at will. Other objects, advantages, and superior features of the present invention are described hereinbelow.

SUMMARY OF THE INVENTION

The present invention provides an improved vapor pressure measurement apparatus and method, particularly adapted for measuring the cavitation pressure and vapor pressure of hydrocarbon liquid compositions.

In accordance with one aspect of the present invention, a vapor pressure measurement apparatus is provided which is characterized by a piston slidable in a cylinder to increase the volume of a chamber formed in the cylinder which is initially filled with a sample of the liquid to be measured. The piston and cylinder arrangement may be automatically controlled to operate through a cycle which will provide readings of cavitation pressure and vapor pressure of a complex liquid mixture such as a mixture of crude petroleum and natural gasoline liquids.

In accordance with another important aspect of the present invention, a vapor pressure measurement apparatus is provided which is adapted to be maintained at a substantially constant temperature, and be continually supplied with a fresh sample of liquid from a liquid stream to be analyzed. The improved apparatus is particularly adapted to minimize errors in the vapor pressure measurement process by the construction of the apparatus in such a way as to minimize trapping of vapor bubbles from the fluid stream prior to the initiation of the measurement process.

In accordance with yet a further aspect of the present invention, an improved vapor pressure measurement apparatus is provided which is adapted for use in petroleum pipelines and other chemical processing operations and may be interconnected in a flow stream of the liquid to be measured without interfering with the main flow of liquid.

The above-mentioned features and advantages of the present invention together with other superior aspects thereof will be further appreciated by those skilled in the art upon reading the detailed description which follows in conjunction with the drawing.

DESCRIPTION OF A PREFERRED EMBODIMENT

Figure 1:
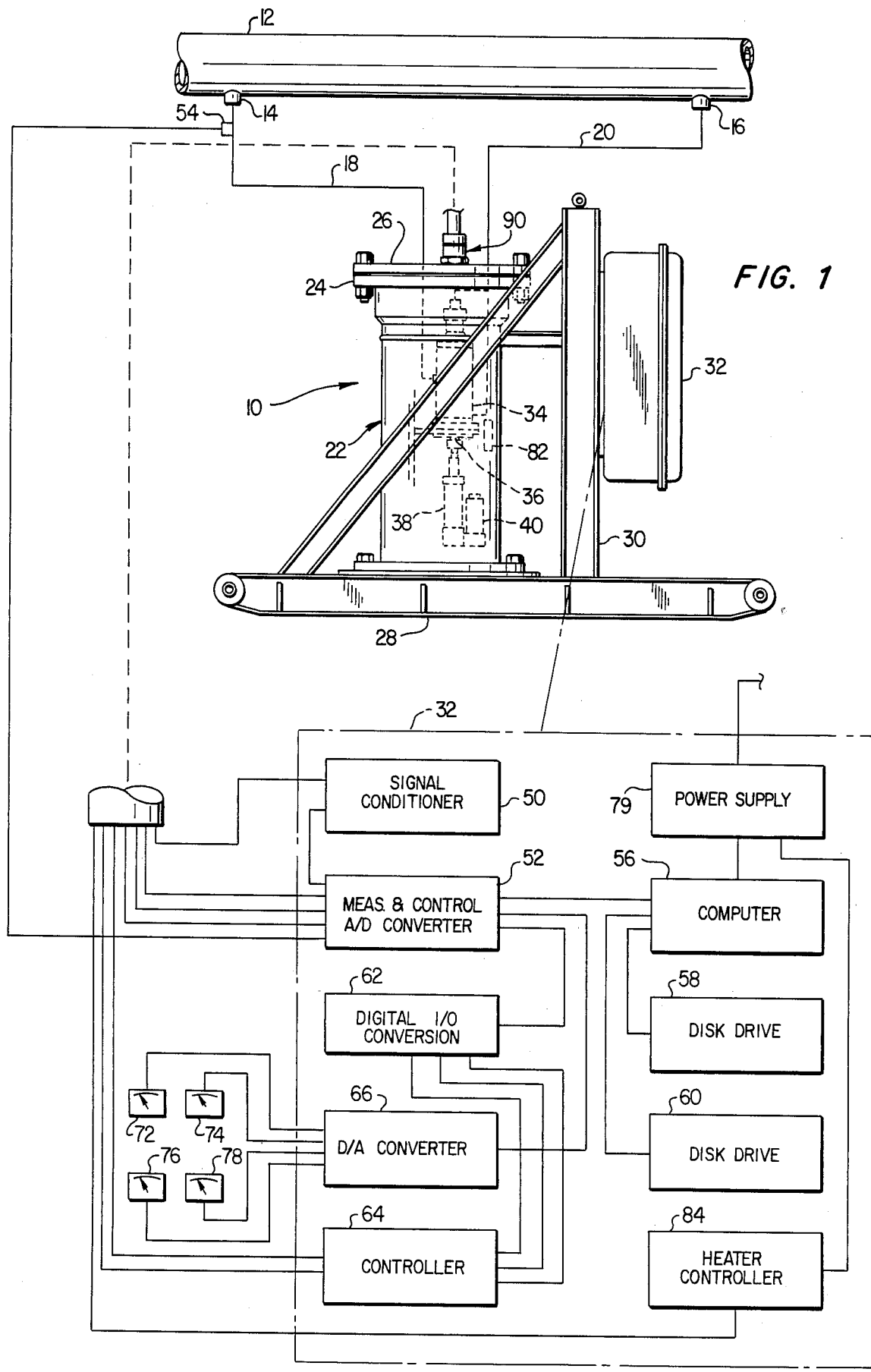
FIG. 1 is a combined side elevation and schematic diagram of the vapor pressure measurement apparatus and system of the present invention.

In the description which follows like parts are marked throughout the specification and drawing with the same reference numerals, respectively. The drawing figures are not necessarily to scale and certain features of the invention may be shown in somewhat schematic form in the interest of clarity and conciseness.

Referring to FIG. 1, there is illustrated a system in accordance with the present invention for measuring the vapor pressure of liquid compositions and mixtures. The system includes apparatus, generally designated by the numeral 10, which is particularly adapted for application to measure vapor pressures in petroleum pipelines, chemical process systems, and the like. For example, there is illustrated a crude oil pipeline 12 which may be a branch line off of a main pipeline system or comprise a main transmission line itself having suitable fittings 14 and 16 for the connection of conduits 18 and 20 leading to and from the apparatus 10. The apparatus 10 is characterized by a closable housing 22 having a transverse upper flange 24 and a removable cover 26. The housing 22 is suitably mounted on a skid 28 for movement to selected test sites, as needed. A support bracket 30 is provided for supporting an enclosure 32 which is adapted to house control circuitry for the apparatus 10 and which is shown in somewhat schematic form in FIG. 1.

The apparatus 10 includes a cylinder housing 34 disposed within the housing 22 and including means defining a bore to be described in further detail herein in which a piston is reciprocal and is connected to a piston rod 36 extending from the cylinder housing. The piston rod 36 is connected to a linear actuator 38 driven by a reversible motor 40 for moving the abovementioned piston to increase or decrease the size of the chamber volume as will also be described in further detail herein.

The control system for the apparatus 10 includes a signal conditioner unit 50 for receiving an electrical signal from a pressure sensing transducer, not shown in FIG. 1, and a measurement and control A/D converter 52 for receiving a conditioned signal from the unit 50 and also for receiving plural electrical signals from a temperature transducer 54 in the conduit 18, a transducer, not shown in FIG. 1, located within the housing 22 and to be described herein and a suitable transducer, not shown, located within the housing 22. A digital computer 56 is adapted to receive signals from the A/D converter 52 for controlling the operation of the apparatus 10, and an operational program disk drive 58 and a data acquisition disk drive 60 are operably connected to the computer 56. The computer 56 and disk drives 58 and 60 are adapted for use in modifying operating characteristics of the system and could be replaced by a suitable microprocessor, now shown. The A/D converter 52 is also operably connected to a digital signal conversion unit 62 which is adapted to effect operation of a control unit 64 for the motor 40. A D/A converter 66 receives signals from the converter 52 and provides suitable pressure and temperature displays through display units 72, 74, 76, and 78. A 120 v a.c. power source, not shown, is connected to and converted to dc power through a suitable power supply unit 79 for operation of the components described above.

The housing 22 also includes a suitable electrical heater 82 disposed therein and controlled by a control unit 84 for maintaining a predetermined temperature of the interior of the housing 22. The signal conductors extending between the housing 22 and the enclosure 32 are preferably routed through a separable multiple pin connector or the like, generally designated by the numeral 90 and having a socket portion 92, FIG. 2, extending through the bulkhead formed by the cover 26. The connector 90 may be of a type commercially available. Commercially available devices corresponding to certain ones of the elements described hereinabove are as follows:

- signal conditioner unit 50 - Model 4428, Endevco Corp.
- A/D converter 52 - Micromac 4000, Analog Devices, Inc., Norwood, MA.
- conversion unit 62 - Micromac 4020, Analog Devices, Inc., Norwood, MA.
- converter 66 - Micromac 4030, Analog Devices, Inc., Norwood, MA.
- actuator 38 - Model 15D electric cylinder Industrial Device, Novato, CA
- controller 64 - Model AC2001 el Industrial Devices
- controller 84 - Model 808, Eurotherm Corp. Reston, VA.

Figure 2:
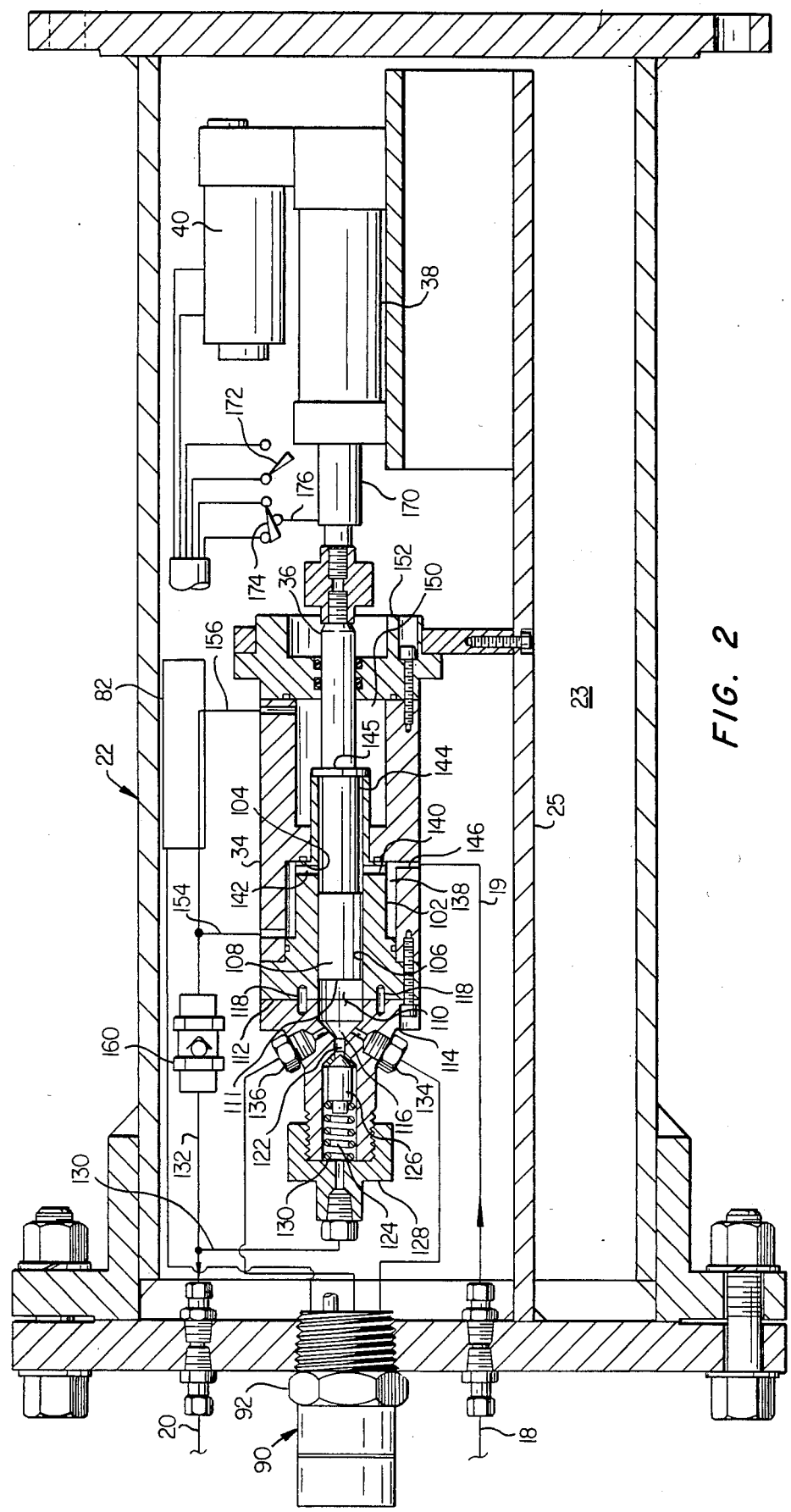
FIG. 2 is a central section view of the vapor pressure measurement apparatus in somewhat schematic form.

Referring now to FIG. 2, certain structural features of the cylinder housing 34 are illustrated in detail. The cylinder housing 34 is suitably supported within the interior space 23 of the housing 22 on a depending support member 25 which is secured to the cover 26 so that the assembly of the cylinder housing 34 and the actuator 38 may be removed from the housing 22. The housing 22 is provided as a protective covering for the apparatus 10 and to minimize the chance of escape of volatile vapors into the atmosphere when the apparatus 10 is utilized to measure the vapor pressure of potentially hazardous substances.

The cylinder housing 34 is preferably characterized by a removable insert part 102 which is mounted within the housing 34 and disposed on a transverse shoulder 104. The insert part 102 includes a cylindrical bore 106 in which a piston 108 is slidably disposed and defines a variable volume chamber 110. The insert part 102 includes a transverse head surface 112 on which a head part 114 is removably bolted in sealed relationship thereto. A portion of the chamber volume 110 may be formed by a cavity 116 in the head part 114. Locating pins 118 are provided for locating the head part 114 on the insert part 102 so that side walls defining the chamber 110 do not have any discontinuities which would provide an area for trapping a vapor bubble. An outlet port 122 is formed in the head part 114 and opens into a chamber 124 in which a spring biased check valve 126 is disposed. A removable cover part 128 retains the check valve 126 and a biasing spring 130 within the chamber 124. A conduit 130 is connected to the cover part 128 and is connected to a further conduit 132 in communication with the return conduit 20 extending to the cover 26. The head part 114 includes suitable cavity for receiving and retaining a pressure transducer 134 of a type commercially available such as a model 8530-50 manufactured by Endevco Corp. of San Juan Capistrano, CA. A temperature sensor 136 is also disposed on the head part 114 for sensing the temperature in the chamber 110. The temperature sensor 136 may also be of a type commercially available such as a type RTD Model PR12 manufactured by Omega Engineering of Stamford, CT.

Referring further to FIG. 2, the cylinder housing 34 and the insert part 102 define therebetween an annular cavity 138 which is in communication with the bore 106 by way of suitable passages 140 and 142 formed in the insert part. An annular groove 144 is formed in the piston 108 between the piston head 111 and an integral collar 145 on the rod 36. The conduit 18, for conducting fluid from the pipeline 12, is in communication with the chamber 138 by way of a passage 146 formed in the cylinder housing 34 and by way of an intermediate conduit 19. A bypass chamber 150 is formed in the cylinder housing 34 between the shoulder 104 and a removable lower head member 152. Return conduits 154 and 156 are in communication with the chambers 138 and 150, respectively, and are connected to the conduits 130, 132 by way of a minimum pressure or pressure relief valve 160. The pressure relief valve 160 is set to allow pressure fluid to flow therethrough but at a pressure nominally greater than the pressure at which the valve 126 will allow fluid to flow through the chamber 110 to the return conduit 130.

Referring still further to FIG. 2, the piston rod 36 is suitably coupled to an actuating rod 170 of the actuator 38 for linear reciprocation of the piston 108 within the bore 106. Position limit switches 172 and 174 are adapted to be operably engaged by a cam 176 on the rod 170 for providing control signals to operate the motor 40 to extend and retract the piston 108 within the bore 106. For example, upon engaging the switch 174 the motor 40 is typically operated to stop extension of the rod 170 and, upon a suitable signal from the control unit 64, the rod 170 may be retracted to move the piston 108 to increase the volume of the chamber 110. A lower limit position of the rod 170 is achieved when the cam 176 engages switch 172.

The apparatus 10 may be operated to determine the cavitation pressure and the vapor pressure of liquid flowing through the pipeline 12, for example, at will, and such vapor pressure measurements are typically carried out at selected time intervals to continuously monitor such pressures of the fluid flowing through the pipeline. A small pressure boost pump, not shown, may be required to be interposed in one of the conduits 18 or 20 to provide for flow of fluid through the apparatus 10. The apparatus 10 is operable to determine the minimum or so called cavitation pressure at which vapor will form as well as what may be considered the true vapor pressure which, for a complex liquid mixture, is normally somewhat greater than the cavitation pressure.

Referring to FIG. 2, in the operation of the apparatus 10 to make a vapor pressure measurement, the piston 108 is normally in a retracted position so that the piston head 111 is disposed below the passages 140 and 142. With fluid being supplied to the conduit 19, it will flow continuously through the chamber 110, across the valve 126 and through the conduit 130, 132 to return to the pipeline 12. By continuously flowing fluid through the chamber 110, the temperature of the apparatus 10, including the cylinder housing 34 and associated parts, is stabilized at the temperature of the fluid from the pipeline 12. When a sample vapor pressure measurement is to be taken, the piston 108 is moved to reduce the volume of the chamber 110 and to momentarily cut off flow of liquid through the conduit 19 as liquid is pushed out of the chamber 110 through the valve 126. When the piston 108 reaches its maximum extended position, corresponding to a minimum volume of chamber 110, groove 144 is placed in communication with the passages 140 and 142 and flow through the chamber formed by the groove 144 provides for the apparatus to maintain a continuous flow of fluid, to minimize the formation of vapor bubbles within the apparatus 10 and to stabilize the temperature of the apparatus. Leakage flow past the piston portion extending between the passages 140, 142 and the chamber 150 maintains this chamber flushed and full of liquid and which flow exits the housing 34 through the conduit 156. This flow also assists in stabilizing the temperature of the components of the apparatus.

The piston 108 is retracted to increase the volume of the chamber 110, without uncovering passages 140 and 142, while pressure measurements are taken as the volume of the chamber 110 increases until the chamber pressure decreases to a relatively constant value with increasing chamber volume, thereby indicating the minimum so called vapor pressure or cavitation pressure of the liquid being analyzed. At this point, the volume of the chamber 110 is held constant for a predetermined period of time and the pressure in the chamber is monitored by the control system to record the characteristic change in pressure with time. The piston 108, in the maximum retracted position during a vapor pressure measurement, must not, of course, retract far enough for the face or head surface 111 to place the passages 140 or 142 in communication with the chamber 110. When a suitable pressure characteristic has been recorded, the piston 108 is then retracted to open the passages 140 and 142 into the chamber 110 to flush the vapor out of the chamber and resume the continuous circulation of liquid through the chamber and back to the pipeline 12. The piston 110 may be maintained in the maximum retracted position until a new vapor pressure measurement is to be taken.

Thanks to the configuration of the piston 108 and the bore 106, there is little likelihood of formation of unwanted vapor bubbles in the chamber 110 except through expansion of the chamber volume to create a bubble due to lowering the pressure to the cavitation and/or true vapor pressure of the liquid mixture being measured. A seal is maintained between the piston 108 and the cylinder wall defining the bore 106 by a very close tolerance fit between the piston and the insert part 102, preferably by utilizing diesel engine fuel injection pump manufacturing techniques and materials. Moreover, the configuration of the chamber 110, which does not have any discontinuous surfaces or grooves, also reduces the likelihood of formation of unwanted vapor bubbles.

During the measurement of cavitation and/or vapor pressure, the temperature in the chamber 110 is continuously monitored by the temperature sensor 136 and this temperature is recorded for each vapor pressure measurement. The controller 84 is operable to cause the heater 82 to maintain either a preset temperature in the space 23 or to maintain the temperature sensed by the sensor 54, whichever is desired.

Figure 3:
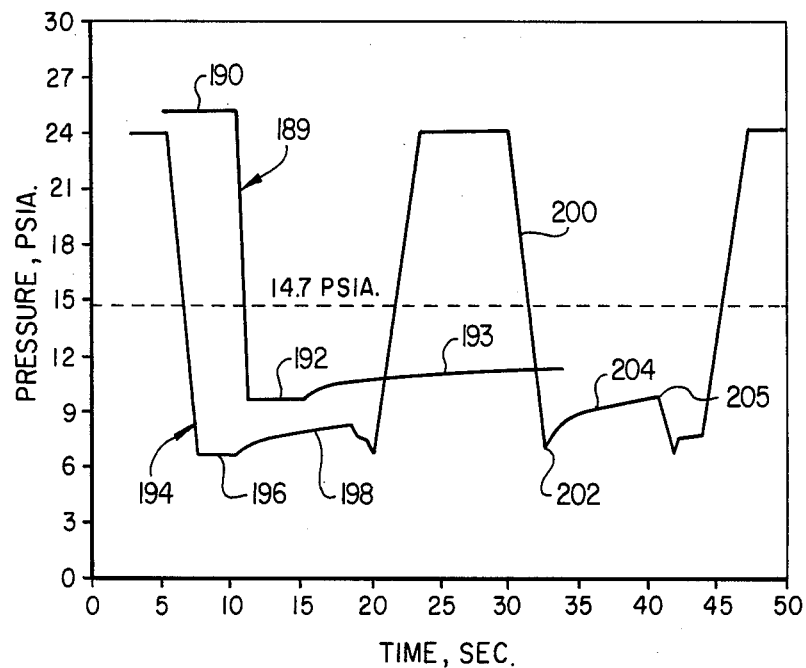
FIG. 3 is a diagram illustrating the total pressure versus time of a fluid sample in the chamber of the measurement apparatus during a cavitation pressure and vapor pressure measurement cycle.

Referring now to FIG. 3, there is illustrated a diagram of the pressure sensed in the chamber 110 during a vapor pressure test of a sample of crude oil in which various natural gasoline liquids have been blended. One pressure time trace 189 includes a steadystate portion 190 which is the pressure sensed in the chamber 110 when the piston 108 is retracted to permit flow of fluid continuously through the chamber from the inlet conduit 19 through the valve 126 to the conduit 130, 132. During this mode of operation, substantially all of the fluid flowing through the cylinder housing 34 will pass through the chamber 110 since the pressure relief setting of the valve 160 is higher than that of the valve 126. When a vapor pressure test is commenced, the piston 108 is extended to decrease the volume of chamber 110 and cut off the flow of fluid into the chamber from passage 140. When the piston 108 reaches a position corresponding to a predetermined minimum volume of chamber 110 the piston is retracted to increase the volume of the chamber 110 until, with increasing volume, there is essentially no change in sensed pressure in the chamber. This condition is represented by the segment 192 of the pressure-time trace 189. After a predetermined time at which there is essentially no change in the pressure sensed in the chamber 110, the computer 56, through the signal converters 60 and 62 causes the controller 64 to effect operation of motor 40 to arrest movement of the piston 108 and the chamber volume is maintained at a constant value. As indicated by the segment 193 of the pressure-time trace, with no change in volume of the chamber 110 there will be a gradual rise in pressure, particularly for liquids which are complex mixtures of more than one liquid or have dissolved gases formed therein. The pressure indicated by the trace segment 193 may be read at a predetermined time as the vapor pressure, which pressure will rise until an equilibrium condition is reached.

The pressure-time trace 194 illustrated in FIG. 3 represents a further test utilizing the apparatus 10 wherein a fluid sample is tested in the apparatus by expanding the volume of the chamber 110 until the cavitation pressure is reached as indicated by the trace segment 196 at which time the volume of the chamber is maintained constant while the pressure increase in the chamber 110 is observed as indicated by the trace segment 198. The chamber 11 is then flushed and a new sample of the same fluid is trapped and the chamber volume expanded as indicated by the trace segment 200 until the cavitation pressure is reached at point 202. Under this second test, however, the volume of the volume chamber 110 is not expanded as much and the pressure rise indicated by the trace segment 204 is to a higher final pressure at point 205.

Figure 4:
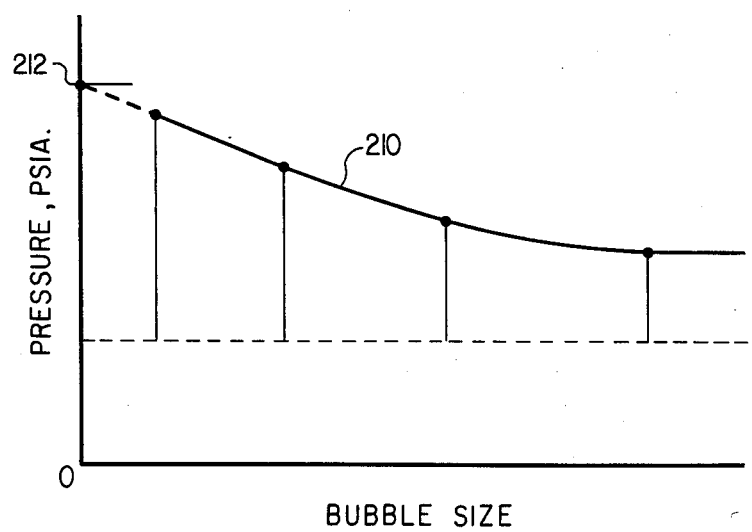
FIG. 4 is a diagram illustrating the expected value of true vapor pressure based on measuring a selected sample at various chamber volumes.

Referring to FIG. 4, there is indicated a comparison of the final equilibrium pressure for a given time period versus the chamber or bubble size. With larger chamber volume for chamber 110 corresponding to a larger vapor bubble volume, the final equilibrium pressure is indicated to be lower for a particular fluid. Accordingly, by plotting a series of final pressures at different chamber or vapor bubble sizes, a trace or curve 210 may be developed which may be extrapolated to indicate the so-called true vapor pressure of a particular liquid mixture at zero bubble size such as indicated at point 212.

Moreover, it has been observed that with complex liquids such as crude petroleum, when a liquid sample expanded in a closed chamber until the cavitation pressure is reached and then the sample is allowed to reach an equilibrium condition that it may require a substantial period of time before a final equilibrium or vapor pressure is reached. However, with the present process two or three liquid samples, which may be taken over a period of a few minutes according to the process described herein, and wherein the equilibrium pressures at various chamber volumes are recorded, may be utilized to extrapolate substantially true vapor pressure. In any case, the minimum pressure which can be tolerated in a system, as indicated by the cavitation or so called bubble point pressure, is readily determined with the method and apparatus of the present invention.

Although preferred embodiments of the invention have been described herein in detail, those skilled in the art will recognize that various substitutions and modifications may be made to the specific embodiments disclosed without departing from the scope and spirit of the invention as recited in the appended claims.

What is claimed is:

1. Apparatus for making measurements of vapor pressure of liquids such as crude petroleum comprising:
    housing means including a cylindrical bore formed therein and defining in part an expansible chamber, said housing means including a head portion closing one end of said bore and including an outlet conduit for conducting fluid out of said chamber;
    valve means disposed in said outlet conduit to prevent the backflow of fluid from said outlet conduit into said chamber;
    an inlet passage in said housing means operable to open to said chamber for conducting fluid to said chamber;
    a reciprocal piston disposed in said bore and movable to a first position to uncover said inlet passage and permit the flow of liquid from said inlet conduit through said chamber and through said outlet conduit on a substantially continuous basis, said piston being movable to close off communication between said inlet passage and said chamber and to reduce the volume of said chamber to a predetermined minimum;
    pressure sensor means in communication with said chamber at said minimum volume position of said piston;
    said piston is disposed in said bore in close fitting relationship thereto to provide seal means between said chamber and said inlet passage, said seal means being formed entirely by a minimum space between said piston and the wall of said housing means defining said bore between said chamber and said inlet passage; and
    actuator means for moving said piston from a first position to provide for admitting fluid to said chamber through said inlet passage to a second position and back toward said first position.

2. The apparatus set forth in claim 1 wherein:
    said housing means includes means defining a bypass flow passage in communication with a second outlet conduit for circulating liquid through said housing means to stabilize the temperature of said apparatus at a temperature related to the temperature of fluid flowing to and from said apparatus.

3. The system set forth in claim 1 wherein:
    said actuator means is associated with control means for moving said piston from said first position to said second position to prevent fluid flowing through said chamber and to reduce the volume of said chamber to a minimum, said control means being operable to move said piston to a third position to increase the volume of said chamber a predetermined amount.

4. A method for determining the vapor pressure of a liquid composition comprising the steps of:
    providing means defining an expansive chamber, said means including passage means adapted to be in communication with said expansible chamber for conducting a liquid sample to be measured to said expansible chamber, and an outlet passage for discharging said liquid sample from said expansible chamber, piston means disposed in said expansible chamber for varying the volume of said expansible chamber between a minimum and a maximum and pressure sensor means in communication with said expansible chamber for monitoring the pressure in said expansible chamber during expansion chamber;
    placing a sample of liquid to be measured in said expansible chamber;
    operating said piston means to move from a predetermined position corresponding to a selected minimum volume of said expansible chamber to a first expansion of said expansible chamber by increasing the volume of said expansible while monitoring the pressure in said expansible chamber to determine when said pressure remains substantially constant with increasing volume of said expansible chamber;
    recording said substantially constant value of pressure corresponding to the cavitation pressure of said liquid;
    replacing said liquid sample in said expansible chamber with another sample of said liquid; and
    causing a second expansion of said expansible chamber to a volume different than the volume of said expansible chamber during said first expansion, and measuring the pressure in said expansible chamber at a predetermined time after arresting said second expansion of said expansible chamber.

5. The method set forth in claim 4 including the steps of:
    comparing a final pressure in said expansible chamber after a predetermined time interval during said first expansion of said expansible chamber with a final pressure in said expansible chamber after a predetermined time interval during said second expansion of said expansible chamber and extrapolating a curve defining said final pressures as a function of the size of said expansible chamber, respectively, to determine a value of vapor pressure of said liquid composition.

6. A method for determining the vapor pressure of a liquid composition comprising the steps of:
providing apparatus comprising a cylinder member including a bore defining an expansible chamber, piston means disposed in said bore for varying the volume of said expansible chamber between a minimum and a maximum, a head portion delimiting one end of said expansible chamber, inlet passage means opening into said bore and operable in response to being covered and uncovered by said piston means to close off communication of liquid to said expansible chamber and to admit liquid to said expansible chamber, respectively, discharge passage means opening into said expansible chamber for conducting liquid out of said expansible chamber, one way valve means interposed in said discharge passage means to prevent the back flow of liquid from said discharge passage means to said expansible chamber, and pressure sensor means in communication with said expansible chamber for monitoring the pressure in said expansible chamber during expansion of said expansible chamber through movement of said piston means in said bore;
placing a sample of liquid to be measured in said expansible chamber by moving said piston means to place said inlet passage means in communication with said expansible chamber;
causing said piston means to move to a position to close off communication of liquid to said expansible chamber through said inlet passage means;
causing said piston means to move to a selected minimum volume condition of said expansible chamber and then to increase the volume of said expansible chamber while monitoring the pressure in said expansible chamber to determine when said pressure remains substantially constant with increasing volume of said expansible chamber; and
recording said substantially constant pressure in said expansible chamber for determining the vapor pressure of said liquid composition.

7. Apparatus for making measurements of vapor pressure of liquids such as crude petroleum comprising:
housing means including a cylindrical bore formed therein and defining in part an expansible chamber, said housing means including a head portion closing one end of said bore and including an outlet conduit for conducting fluid out of said expansible chamber, valve means disposed in said outlet conduit to prevent the backflow of fluid from said outlet conduit into said expansible chamber, inlet passage means in said housing means opening to said expansible chamber and adapted to be in communication with an inlet conduit for conducting fluid to said expansible chamber;
a reciprocal piston disposed in said bore and movable to a first position to uncover said inlet passage means and permit the flow of liquid from said inlet conduit through said expansible chamber and through said outlet conduit, said piston being movable to close off communication between said inlet passage and said expansible chamber and to a position to reduce the volume of said expansible chamber to a predetermined minimum;
actuator means for moving said piston from said first position to a second position comprising a minimum volume of said expansible chamber and back toward said first position; and
bypass passage means formed in said housing means in communication with said inlet conduit for circulation of liquid through said housing means when said piston has moved to close off said inlet passage means, and a second outlet conduit for conducting flow of fluid from said bypass passage means out of said housing means to stabilize the temperature of said housing means during operation of said apparatus to measure the vapor pressure of a liquid sample.

8. Apparatus for making measurements of vapor pressure of liquids such as crude petroleum comprising:
housing means including a cylindrical continuous bore of substantially constant diameter formed therein and defining in part an expansible chamber, said housing means including a separable head portion closing one end of said bore and including an outlet conduit for conducting fluid out of said expansible chamber, means for aligning said separable head portion with said housing means to minimize surface discontinuities in a portion of said bore defining said expansible chamber, valve means disposed in said outlet conduit to prevent the backflow of fluid from said outlet conduit into said expansible chamber, inlet passage means in said housing means opening to said expansible chamber and adapted to be in communication with an inlet conduit for conducting fluid to said expansible chamber;
a reciprocal piston disposed in said bore and movable to a first position to uncover said inlet passage means and permit the flow of liquid from said inlet conduit through said expansible chamber and through said outlet conduit, said piston being movable to close off communication between said inlet passage means and said chamber and to a position to reduce the volume of said expansible chamber to a predetermined minimum;
seal means formed solely by a close fitting relationship between said piston and said bore to minimize surface discontinuities in said expansible chamber between said inlet passage means and said outlet conduit;
pressure sensor means in communication with said expansible chamber at said minimum volume position of said piston;
actuator means for moving said piston from said first position to a second position comprising said minimum volume of said expansible chamber and back toward said first position; and
control means form moving said piston to trap a sample of liquid in said expansible chamber, and to expand said expansible chamber until the pressure in said expansible chamber sensed by said sensor means is reduced to a predetermined amount and remains substantially unchanged with increasing volume of said expansible chamber whereby at least the cavitation pressure of a liquid sample trapped in said expansible chamber may be determined.

9. The apparatus set forth in claim 8 wherein:
said housing means includes passage means formed therein for circulation of liquid through said housing means when said piston has moved to close off said inlet passage means, and a second outlet conduit for conducting flow of liquid through said housing means and out of said housing means substantially uninterrupted during operation of said apparatus to measure the vapor pressure of a liquid sample.

10. The apparatus set forth in claim 8 wherein:
said actuator means includes motor means for moving said piston from a first position which admits liquid to said expansible chamber to a second position which closes off said inlet passage and reduces the volume of said expansible chamber to a minimum and to a third position corresponding to a volume of said expansible chamber at which the pressure in said expansible chamber has decreased to at least the cavitation pressure of said liquid.

* * * * *